United States Patent
Souda et al.

(10) Patent No.: US 8,779,222 B2
(45) Date of Patent: Jul. 15, 2014

(54) METHOD FOR PRODUCING 1,1,3-TRICHLORO-1-PROPENE

(75) Inventors: Hiroshi Souda, Oita (JP); Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 187 days.

(21) Appl. No.: 13/389,168

(22) PCT Filed: Aug. 27, 2010

(86) PCT No.: PCT/JP2010/065082
§ 371 (c)(1),
(2), (4) Date: Feb. 6, 2012

(87) PCT Pub. No.: WO2011/025063
PCT Pub. Date: Mar. 3, 2011

(65) Prior Publication Data
US 2012/0142981 A1    Jun. 7, 2012

(30) Foreign Application Priority Data
Aug. 31, 2009   (JP) .................................. 2009-199763

(51) Int. Cl.
*C07C 17/25* (2006.01)
*C07C 17/358* (2006.01)

(52) U.S. Cl.
CPC ............... *C07C 17/25* (2013.01); *C07C 17/358* (2013.01)
USPC ......................................... 570/228; 570/236

(58) Field of Classification Search
USPC ................................................. 570/228, 236
See application file for complete search history.

(56) References Cited

U.S. PATENT DOCUMENTS

| 2,561,516 A | 7/1951 | Ladd |
| 4,535,194 A * | 8/1985 | Woodard ...................... 570/236 |
| 4,650,914 A | 3/1987 | Woodard |

FOREIGN PATENT DOCUMENTS

| CA | 1234157 A2 * | 3/1988 |
| JP | 49-066613 A | 6/1974 |
| JP | 60-036429 A | 2/1985 |
| JP | 08-245439 A | 9/1996 |

OTHER PUBLICATIONS

Shakhnazaryan, G. M. (Armyanskii Khimicheskii Zhurnal, vol. 36, Issue: 8, pp. 504-508; Abstract only).*
Int'l Preliminary Report on Patentability issued Mar. 15, 2012 in Int'l Application No. PCT/JP2010/065082.
Int'l Search Report issued Sep. 28, 2010 in Int'l Application No. PCT/JP2010/065082.
Haszeldine, "Fluoro-olefins. Part II. Synthesis and Reactions of Some 3:3:3-Trihalogenopropenes," Journal of the Chemical Society, vol. 1953, pp. 3371-3378 (1953).

* cited by examiner

*Primary Examiner* — Jafar Parsa
*Assistant Examiner* — Medhanit Bahta
(74) *Attorney, Agent, or Firm* — Panitch Schwarze Belisario & Nadel LLP

(57) ABSTRACT

A production method of 1,1,3-trichloro-1-propene comprising the following steps A and B;
Step A: 1,1,1,3-tetrachloropropane is dehydrochlorinated at a temperature between 30° C. and 50° C. in the presence of at least one base selected from the group consisting of alkali metal hydroxides and alkaline earth metal hydroxides, and a phase transfer catalyst,
Step B: 3,3,3-trichloro-1-propene obtained in the step A is isomerized into 1,1,3-trichloro-1-propene in the presence of a metal catalyst.

19 Claims, No Drawings

METHOD FOR PRODUCING 1,1,3-TRICHLORO-1-PROPENE

CROSS-REFERENCE TO RELATED APPLICATIONS

This application is a Section 371 of International Application No. PCT/JP2010/065082, filed Aug. 27, 2010, which was published in the Japanese language on Mar. 3, 2011, under International Publication No. WO 2011/025063 A1 and the disclosure of which is incorporated herein by reference.

BACKGROUND OF THE INVENTION

1. Technical Field

The present invention relates to a production method of 1,1,3-trichloro-1-propene.

2. Background Art 1,1,3-trichloro-1-propene is useful as a synthesis intermediate of agricultural chemicals, medicines and the like. As the production method thereof, for example, a method of heating 1,1,1,3-tetrachloropropane at 80 to 95° C. in the presence of iron chloride is described in JP-A No. 49-66613 (examples).

BRIEF SUMMARY OF THE INVENTION

The instant application relates to the following inventions.

[1] A production method of 1,1,3-trichloro-1-propene comprising the following steps A and B;

Step A: 1,1,1,3-tetrachloropropane is dehydrochlorinated at a temperature between 30° C. and 50° C. in the presence of at least one base selected from the group consisting of alkali metal hydroxides and alkaline earth metal hydroxides, and a phase transfer catalyst, Step B: 3,3,3-trichloro-1-propene obtained in the step A is isomerized into 1,1,3-trichloro-1-propene in the presence of a metal catalyst.

[2] A production method of 1,1,3-trichloro-1-propene comprising the following steps A and B;

Step A: 1,1,1,3-tetrachloropropane is dehydrochlorinated at a temperature between 30° C. and 50° C. in the presence of at least one base selected from the group consisting of alkali metal hydroxides and alkaline earth metal hydroxides, and a phase transfer catalyst, to obtain a mixture containing 1,1,3-trichloro-1-propene and 3,3,3-trichloro-1-propene;

Step B: the mixture containing 1,1,3-trichloro-1-propene and 3,3,3-trichloro-1-propene is allowed to contact with a metal catalyst, to isomerize 3,3,3-trichloro-1-propene in the above-described mixture into 1,1,3-trichloro-1-propene.

[3] The production method according to [1] or [2], wherein the phase transfer catalyst is a quaternary ammonium salt or a quaternary phosphonium salt.

[4] The production method according to [1] or [2], wherein a base aqueous solution is used as the base in the step A.

[5] The production method according to any one of [1] to [4], wherein a step C is carried out between the step A and the step B;

Step C: the reaction mixture obtained in the step A is washed with an acid, then washed with water.

[6] The production method according to [5], wherein the acid is hydrochloric acid, sulfuric acid, phosphoric acid or nitric acid.

[7] The production method according to any one of [1] to [6], wherein the metal catalyst is a metal simple body or a metal compound containing at least one metal selected from the group consisting of group VII metals, group VIII metals, group IX metals, group X metals, group XI metals, group XII metals, group XIV metals and group XV metals in the periodic table.

[8] The production method according to any one of [1] to [7], wherein the metal catalyst is a metal simple body or a metal compound containing at least one metal selected from the group consisting of iron, copper, zinc, silver, nickel, palladium, tin, bismuth and manganese.

[9] The production method according to any one of [1] to [8], wherein isomerization in the step B is carried out under a temperature between 50° C. and 120° C.

[10] The production method according to any one of [1] to [9], wherein the step A is carried out in the absence of an organic solvent.

[11] The production method according to any one of [1] to [10], wherein the step B is carried out in the absence of an organic solvent.

[12] A production method of 1,1,3-trichloro-1-propene, comprising a step of dehydrochlorinating 1,1,1,3-tetrachloropropane under a temperature between 30° C. and 50° C. in the presence of at least one base selected from the group consisting of alkali metal hydroxides and alkaline earth metal hydroxides, and a phase transfer catalyst.

DETAILED DESCRIPTION OF PREFERRED EMBODIMENTS

The present invention will be illustrated in detail below.

The production method of the present invention comprises the step A, preferably comprises the step A and the step B.

In the present invention, the step A is a step of dehydrochlorinating 1,1,1,3-tetrachloropropane at a temperature between 30° C. and 50° C., that is, a temperature of 30° C. or higher and 50° C. or lower in the presence of at least one base selected from the group consisting of alkali metal hydroxides and alkaline earth metal hydroxides, and a phase transfer catalyst.

The above-described phase transfer catalyst is a compound having a phase transferring ability. The above-described phase transfer catalyst includes quaternary ammonium salts, quaternary phosphonium salts, amine N-oxides, crown ethers, polyethylene glycols and the like.

The quaternary ammonium salts include quaternary ammonium chlorides such as trioctylmethylammonium chloride, trioctylethylammonium chloride, dilauryldimethylammonium chloride, lauryltrimethylammonium chloride, stearyltrimethylammonium chloride, lauryldimethylbenzylammonium chloride, tricaprylmethylammonium chloride, tridecylmethylammonium chloride, trihexylmethylammonium chloride, tridecylmethylammonium chloride, tetrabutylammonium chloride, benzyltrimethylammonium chloride, benzyltriethylammonium chloride, N-laurylpyridinium chloride, N-cetylpyridinium chloride, N-laurylpicolinium chloride and the like, quaternary ammonium bromides such as trioctylmethylammonium bromide, trioctylethylammonium bromide, dilauryldimethylammonium bromide, lauryltrimethylammonium bromide, stearyltrimethylammonium chloride, lauryldimethylbenzylammonium bromide, tricaprylmethylammonium bromide, tridecylmethylammonium bromide, trihexylmethylammonium bromide, tridecylmethylammonium bromide, tetrabutylammonium bromide, benzyltrimethylammonium bromide, benzyltriethylammonium bromide, N-laurylpyridinium bromide, N-cetylpyridinium bromide, N-laurylpicolinium bromide and the like, quaternary ammonium iodides obtained by substituting a chlorine ion constituting the above-described quaternary ammonium chlorides by an iodine ion, quaternary ammonium sulfites obtained by substituting a chlorine ion constituting the above-described quaternary ammonium chlorides by a sulfite ion, quaternary ammonium sulfates obtained by substituting a chlorine ion constituting the above-described quaternary ammonium chlorides by a sulfate ion, quaternary ammonium hydrogen sulfates obtained by substituting a chlorine ion constituting the above-described quaternary ammonium chlorides by a hydrogen sulfate ion, and the like.

The quaternary phosphonium salts include quaternary phosphonium chlorides such as tributylmethylphosphonium chloride, triethylmethylphosphonium chloride, butyltriphenylphosphonium chloride, tetrabutylphosphonium chloride, benzyltriphenylphosphonium chloride, hexadecyltrimethylphosphonium chloride, hexadecyltributylphosphonium chloride and the like, quaternary phosphonium bromides obtained by substituting a chlorine ion constituting the above-described quaternary phosphonium chlorides by a bromine ion, quaternary phosphonium iodides obtained by substituting a chlorine ion constituting the above-described quaternary phosphonium chlorides by an iodine ion, and the like.

The amine N-oxides include trioctylamine N-oxide, dilaurylmethylamine N-oxide, lauryldimethylamine N-oxide, stearyldimethylamine N-oxide, tricaprylamine N-oxide, tridecylamine N-oxide, dimethyldodecylamine N-oxide, trihexylamine N-oxide, tridodecylamine N-oxide, benzyldimethylamine N-oxide, benzyldiethylamine N-oxide and the like.

The crown ethers include 12-crown-4, 18-crown-6, benzo-18-crown-6 and the like.

The polyethylene glycols include polyethylene glycol 600 (the average molecular weight: approximately 600), polyethylene glycol 700 (the average molecular weight: approximately 700), polyethylene glycol 800 (the average molecular weight: approximately 800) and the like.

The phase transfer catalysts include preferably quaternary ammonium salts and quaternary phosphonium salts, more preferably quaternary ammonium salts, further preferably quaternary ammonium bromides.

As the above-described quaternary ammonium bromide, tetraalkyl ammonium bromides are preferable. The carbon atom number of each alkyl group in the above-described tetraalkyl ammonium bromides is preferably 1 to 10.

The amount of the phase transfer catalyst in the step A is preferably 0.0001 mol or more, more preferably 0.0005 mol to 0.1 mol, further preferably in the range of 0.001 to 0.1 mol, with respect to 1 mol of 1,1,1,3-tetrachloropropane.

The phase transfer catalyst may be any of commercially available compounds and those prepared by known methods.

The base in the step A is selected from the group consisting of alkali metal hydroxides and alkaline earth metal hydroxides. The above-described alkali metal hydroxides include lithium hydroxide, sodium hydroxide, potassium hydroxide and the like. The above-described alkaline earth metal hydroxides include magnesium hydroxide, calcium hydroxide and the like.

The above-described base includes preferably alkali metal hydroxides, more preferably sodium hydroxide and potassium hydroxide.

In the step A, the amount of the base is usually 1 mol or more, preferably in the range of 1.05 to 10 mol, with respect to 1 mol of 1,1,1,3-tetrachloropropane.

As the base in the step A, a base aqueous solution is preferably used. The base aqueous solution is generally composed of water and the base as exemplified above.

The concentration of the base in the above-described base aqueous solution is usually in the range of 5 to 50 wt %.

The above-described base aqueous solution may be a commercially available product, or may be prepared from a commercially available solid base and water.

The amount of the above-described base aqueous solution may advantageously be in the range in which the amount of a base in the aqueous solution meets the above-described amount of the base.

The step A may be carried out in the absence of an organic solvent, or may be carried out in the presence of an organic solvent which does not disturb dehydrochlorination.

The above-described organic solvent includes ether solvents such as diethyl ether, methyl tert-butyl ether, tetrahydrofuran, dioxane, diisopropyl ether and the like; aromatic hydrocarbon solvents such as toluene, xylene and the like; aliphatic hydrocarbon solvents such as hexane, heptane and the like; etc.

The use amount of the organic solvent is not particularly restricted, and if volumetric efficiency and the like are taken into consideration, the use amount is practically 100 parts by weight or less, preferably 20 parts by weight or less, with respect to 1 part by weight of 1,1,1,3-tetrachloropropane.

The step A is preferably carried out in the absence of an organic solvent.

The mixing order of 1,1,1,3-tetrachloropropane, the phase transfer catalyst and the base in the step A is not particularly restricted.

The step A is carried out at a temperature between 30° C. and 50° C.

By performing the step A, a mixture containing 1,1,3-trichloro-1-propene and 3,3,3-trichloro-1-propene is obtained, and by condensation of 3,3,3-trichloro-1-propene, high boiling point compounds such as a dimer of 3,3,3-trichloro-1-propene, and the like can be produced as by-products.

Since dehydrochlorination is carried out at a temperature of 30° C. or higher in the step A, the amount of unreacted 1,1,1,3-tetrachloropropane can be reduced. Further, since dehydrochlorination is carried out at a temperature of 50° C. or lower in the step A, generation of the above-described high boiling point compounds is suppressed and the total yield of 1,1,3-trichloro-1-propene and 3,3,3-trichloro-1-propene can be improved.

The step A is carried out preferably by mixing 1,1,1,3-tetrachloropropane and a phase transfer catalyst, keeping the resultant mixture at a temperature in the range of 30° C. or higher and 50° C. or lower, then, mixing the above-described mixture and a base while maintaining the above-described temperature range.

The step A is preferably carried out under a normal pressure condition, however, it may also be carried out under a pressurized condition.

The reaction time of the step A is appropriately determined by confirming the amount of 1,1,1,3-tetrachloropropane, 1,1,3-trichloro-1-propene or 3,3,3-trichloro-1-propene, by an analysis means such as, for example, gas chromatography, liquid chromatography and the like. The reaction time of the step A is usually in the range of 10 minutes to 24 hours.

In the production method of the present invention, it is preferable that a step C is carried out between the step A and the step B.

Step C: the reaction mixture obtained in the step A is washed with an acid, then washed with water.

In the above-described step C, mineral acids such as hydrochloric acid, sulfuric acid, phosphoric acid, nitric acid and the like are mentioned as the acid. As the acid in the above-described step C, an aqueous solution of an acid may also be used.

When a base aqueous solution is used as the base in the step A, the step C can be carried out, for example, as described below.

A step in which an aqueous layer is separated from the above-described mixture, then, the resultant organic layer is washed with an acid, then washed with water.

A step in which the above-described mixture is washed with an acid, an aqueous layer is removed from the resultant mixed solution, then the resultant organic layer is washed with water.

In the step C, the separated aqueous layer and an organic solvent may be mixed, thereby extracting 1,1,3-trichloro-1-propene and 3,3,3-trichloro-1-propene in the aqueous layer into the organic solvent. The above-described organic solvent is not restricted, and includes the above-described ether solvents, aromatic hydrocarbon solvents, aliphatic hydrocarbon solvents and the like.

Next, the step B will be illustrated.

In the step B, 3,3,3-trichloro-1-propene obtained in the step A is isomerized into 1,1,3-trichloro-1-propene in the presence of a metal catalyst.

The step B can be carried out usually by allowing a mixture containing 1,1,3-trichloro-1-propene and 3,3,3-trichloro-1-propene to contact with a metal catalyst.

As the mixture, a mixture obtained in the above-described step A may be used as it is, or a mixture obtained in the step C may also be used. As the above-described mixture, two or more mixtures having mutually different contents of 3,3,3-trichloro-1-propene and the like may be mixed and used. The mixture containing 1,1,3-trichloro-1-propene and 3,3,3-trichloro-1-propene may be subjected to a purification operation such as distillation and the like before being used in the step B.

The above-described metal catalyst is usually a metal simple body or a metal compound.

The metal constituting the above-described metal simple body or metal compound includes group VII metals of the periodic table such as manganese, rhenium and the like; group VIII metals such as iron, ruthenium and the like; group IX metals such as cobalt, rhodium and the like; group X metals such as nickel, palladium, platinum and the like; group XI metals such as copper, silver and the like; group XII metals such as zinc and the like; group XIV metals such as tin, lead and the like; and group XV metals such as antimony, bismuth and the like.

The above-described metal compound includes metal oxides; metal halides such as metal chlorides, metal bromides and the like; metal sulfides; mineral acid salts of metals such as metal nitrates, metal sulfates, metal phosphates and the like; carbonyl complexes, and the like.

The above-described metal catalyst may form a complex with other compounds, or a hydrate with other compounds such as a hydrate of an iron halide and the like.

Examples of the metal compound containing a group VII metal include manganese oxide, manganese chloride, methyl rhenium trioxide, rhenium oxide, rhenium chloride and the like.

Examples of the metal compound containing a group VIII metal include ferrous chloride and a hydrate thereof, ferric chloride and a hydrate thereof, ferrous bromide and a hydrate thereof, ferric bromide and a hydrate thereof, ferrous oxide, ferric oxide, iron nitrate and a hydrate thereof, iron acetylacetonate complex, iron carbonyl complex, ruthenium chloride, ruthenium oxide and the like.

Examples of the metal compound containing a group IX metal include cobalt oxide, cobalt chloride, rhodium chloride, rhodium oxide and the like.

Examples of the metal compound containing a group X metal include nickel oxide, palladium oxide, palladium chloride and the like.

The metal compound containing a group XI metal includes cuprous oxide (copper (I) oxide), cupric oxide (copper (II) oxide), silver metal, silver oxide and the like.

The metal compound containing a group XII metal includes zinc oxide, zinc bromide, zinc chloride and the like.

The metal compound containing a group XIV metal includes tin oxide, tin chloride, lead oxide and the like.

The metal compound containing a group XV metal includes antimony oxide, antimony chloride, bismuth oxide, bismuth chloride and the like.

The above-described metal catalyst is preferably a metal simple body or a metal compound containing at least one metal selected from the group consisting of group VII metals, group VIII metals, group IX metals, group X metals, group XI metals, group XII metals, group XIV metals and group XV metals in the periodic table, more preferably a metal simple body or a metal compound containing at least one metal selected from the group consisting of iron, copper, zinc, silver, nickel, palladium, tin, bismuth and manganese.

The metal catalyst may be used singly, or two or more metal catalysts may be used in admixture.

The metal catalyst may be used as it is, or may be supported on a carrier such as, for example, activated carbon, silica, alumina, titania, zeolite and the like.

When the metal catalyst is used as it is, those having a smaller particle size are preferable.

Specific examples of the metal catalyst include, preferably, iron; iron compounds such as ferrous chloride and a hydrate thereof, ferric chloride and a hydrate thereof, ferrous bromide and a hydrate thereof, ferric bromide and a hydrate thereof, ferrous oxide, ferric oxide, iron nitrate and a hydrate thereof, iron acetylacetonate complex, iron carbonyl complex and the like; copper; copper compounds such as cuprous oxide, cupric oxide and the like; zinc; zinc compounds such as zinc oxide, zinc bromide, zinc chloride and the like; silver; silver compounds such as silver oxide and the like; nickel; nickel compounds such as nickel oxide and the like; palladium; palladium compounds such as palladium oxide, palladium chloride and the like; manganese; manganese compounds such as manganese oxide, manganese chloride and the like; tin; tin compounds such as tin oxide, tin chloride and the like; bismuth; and bismuth compounds such as bismuth oxide, bismuth chloride and the like, more preferably, iron and iron compounds such as ferrous chloride hydrate, ferric chloride hydrate, ferrous oxide, ferric oxide, iron nitrate hydrate and the like; copper and copper compounds such as cuprous oxide, cupric oxide and the like; zinc and zinc compounds such as zinc oxide, zinc chloride and the like; silver; nickel; palladium; manganese; tin; and bismuth, further preferably, iron, ferrous chloride, copper, zinc and zinc dichloride, particularly preferably, iron, copper and zinc.

The amount of the metal catalyst is usually 0.0001 mol or more, preferably in the range of 0.01 to 1 mol, with respect to 1 mol of 3,3,3-trichloro-1-propene.

The step B may be carried out in the presence of an organic solvent which does not disturb isomerization, or may be carried out in the absence of the above-described organic solvent.

As the above-described organic solvent, exemplified are organic solvents listed as the organic solvent in the step A, and preferably, it is the same solvent as used in the step A.

The use amount of the organic solvent is not particularly restricted, and if volumetric efficiency and the like are taken into consideration, it is practically 100 parts by weight or less, preferably 20 parts by weight or less, with respect to 1 part by weight of 1,1,1,3-tetrachloropropane. The step B is carried out, further preferably, in the absence of an organic solvent.

Isomerization in the step B is usually carried out at a temperature between 0 and 150° C., preferably between 50 and 120° C., more preferably between 60 and 100° C.

When the above-described temperature is 0° C. or higher, the yield of 1,1,3-trichloro-1-propene can be improved, while when the above-described temperature is 150° C. or lower, generation of high boiling point compounds can be suppressed.

Further specifically, in the step B, for example, a mixture containing 1,1,3-trichloro-1-propene and 3,3,3-trichloro-1-propene can be contacted with the metal catalyst under normal pressure or under pressurization in the above-described temperature range, thereby isomerizing 3,3,3-trichloro-1-propene into 1,1,3-trichloro-1-propene.

The contact time of the above-described mixture with the metal catalyst is appropriately determined by confirming the amount of 1,1,3-trichloro-1-propene, 1,1,1,3-trichloro-1-propene or 3,3,3-trichloro-1-propene by an analysis means such as, for example, gas chromatography, liquid chromatography and the like. The contact time is usually in the range of 10 minutes to 24 hours.

Since the reaction mixture after completion of contact contains insoluble components such as the metal catalyst and the like in addition to 1,1,3-trichloro-1-propene, it is preferable to remove insoluble components such as the metal catalyst and the like from the reaction mixture by filtration and the like. Before or after removal of insoluble components such as the metal catalyst and the like, the above-described reaction mixture may be, if necessary, washed or neutralized with water, acid, base or the like.

Further, when the step A and/or the step B is carried out in the presence of an organic solvent, the above-described reaction mixture can also be condensed, thereby isolating 1,1,3-trichloro-1-propene. 1,1,3-trichloro-1-propene may also be purified by a purification means such as distillation, column chromatography and the like.

The insoluble components containing the metal catalyst and the like removed from the reaction mixture can be, as they are, re-used as the metal catalyst in the step B, or can be washed with the above-described organic solvent, water, acid, base or the like before being re-used as the metal catalyst.

DETAILED DESCRIPTION OF THE INVENTION

EXAMPLES

The present invention will be illustrated further in detail by examples below. % is by weight unless otherwise stated.

Example 1

Into a 3 L flask equipped with a reflux condenser were charged 800 g of 1,1,1,3-tetrachloropropane, 1200 g of a 20% sodium hydroxide aqueous solution and 0.8 g of tetrabutylammonium bromide, and a temperature rising operation was performed up to an internal temperature of 45° C. The mixture was stirred at the same temperature for 13 hours to confirm approximate disappearance of 1,1,1,3-tetrachloropropane by gas chromatography, thus, this reaction solution was cooled down to a room temperature of approximately 25° C.

This reaction solution was allowed to stand still, to cause separation into two layers. Of them, the upper layer was recovered, and 240 g of a 5% sulfuric acid aqueous solution was added to the upper layer, and the mixture was stirred for 10 minutes, then, allowed to stand still, to cause separation into two layers. Of them, the upper layer was washed with 240 g of water, to obtain 627 g of a mixture containing 1,1,3-trichloro-1-propene and 3,3,3-trichloro-1-propene. The mixture was subjected to composition analysis by a gas chromatography area percentage method.

Composition of Mixture
1,1,3-trichloro-1-propene: 39.5%
3,3,3-trichloro-1-propene: 56.0%
Dimer of 3,3,3-trichloro-1-propene (hereinafter, referred to as a high boiling point compound in some cases): 2.3%
1,1,1,3-tetrachloropropane: 2.2%
(Yield: the total amount of 1,1,3-trichloro-1-propene and 3,3,3-trichloro-1-propene) 91.5%

Example 2

The same procedure as in Example 1 was carried out excepting that the reaction temperature was 40° C. and the reaction time was 28 hours, thereby obtaining 623 g of a mixture containing 1,1,3-trichloro-1-propene and 3,3,3-trichloro-1-propene. The mixture was subjected to composition analysis by the same method as in Example 1, to find the yield.

Composition of Mixture
1,1,3-trichloro-1-propene: 39.9%
3,3,3-trichloro-1-propene: 55.9%
High boiling point compound: 3.1%
1,1,1,3-tetrachloropropane: 1.2%
(Yield: the total amount of 1,1,3-trichloro-1-propene and 3,3,3-trichloro-1-propene) 90.4%

Example 3

The same procedure as in Example 1 was carried out excepting that the reaction temperature was 35° C. and the reaction time was 42 hours, thereby obtaining 625 g of a mixture containing 1,1,3-trichloro-1-propene and 3,3,3-trichloro-1-propene. The mixture was subjected to composition analysis by the same method as in Example 1, to find the yield.

Composition of Mixture
1,1,3-trichloro-1-propene: 39.2%
3,3,3-trichloro-1-propene: 56.8%
High boiling point compound: 2.7%
1,1,1,3-tetrachloropropane: 1.3%
(Yield: the total amount of 1,1,3-trichloro-1-propene and 3,3,3-trichloro-1-propene) 90.9%

Example 4

The same procedure as in Example 1 was carried out excepting that the reaction temperature was 50° C. and the reaction time was 9 hours, thereby obtaining 624 g of a mixture containing 1,1,3-trichloro-1-propene and 3,3,3- trichloro-1-propene. The mixture was subjected to composition analysis by the same method as in Example 1, to find the yield.

Composition of Mixture
1,1,3-trichloro-1-propene: 39.9%
3,3,3-trichloro-1-propene: 55.7%
High boiling point compound: 2.6%
1,1,1,3-tetrachloropropane: 1.7%
(Yield: the total amount of 1,1,3-trichloro-1-propene and 3,3,3-trichloro-1-propene) 89.3%

Example 5

Into a 500 ml flask equipped with a reflux condenser were charged 300 g of the mixture obtained in Example 1 (the total content of 1,1,3-trichloro-1-propene and 3,3,3-trichloro-1-propene is 93.3%) and 0.3 g of zinc chloride [ZnCl2], and the mixture was heated up to 90° C., then, stirred at the same temperature for 6 hours.

This reaction solution was cooled down to room temperature, then, 120 g of a 5% sodium hydroxide aqueous solution was added, and the mixture was stirred for 10 minutes, then, allowed to stand still, to cause separation into two layers. Of them, the upper layer was recovered, 120 g of a 5% sulfuric acid aqueous solution was added to the upper layer, and the mixture was stirred for 10 minutes, then, allowed to stand still, to cause separation into two layers. Of them, the upper layer was recovered, and the upper layer was washed with 120 g of water, to obtain 303 g of a coarse product of 1,1,3-trichloro-1-propene. The solution was subjected to composition analysis by a gas chromatography internal standard method.

(Composition) 1,1,3-trichloro-1-propene content: 91.5%
(Yield) 97.2%

The above-described yield is represented by (the amount of 1,1,3-trichloro-1-propene×100)/(the total amount of 1,1,3-trichloro-1-propene and 3,3,3-trichloro-1-propene in a mixture used in the reaction).

(hereinafter, the same shall apply to yields in Example 6 to 19)

This coarse product (285 g) was charged in a distillation apparatus, and 261 g of a fraction was obtained at a pressure reduction degree of 10 kPa and an overhead temperature of 60° C. to 67° C. This fraction was subjected to composition analysis by a gas chromatography internal standard method.

(Composition) content of 1,1,3-trichloro-1-propene: 95.4%
(Distillation yield) 95.6%

The above-described distillation yield is represented by (the amount of 1,1,3-trichloro-1-propene×100)/(the amount of 1,1,3-trichloro-1-propene in the coarse product).

Example 6

A mixture containing 1,1,3-trichloro-1-propene and 3,3,3-trichloro-1-propene (1,1,3-trichloro-1-propene content: 41%, 3,3,3-trichloro-1-propene content: 59%) was prepared by the same method as in Examples 1 to 4.

Into a 100 mL flask equipped with a reflux condenser were charged 10 g of the resultant mixture and 0.1 g of an iron powder, and the mixture was heated up to 90° C., then, stirred at the same temperature for 8 hours. The resultant reaction mixture was cooled down to room temperature, then, the solution was subjected to composition analysis by a gas chromatography internal standard method.

(Composition) 1,1,3-trichloro-1-propene:3,3,3-trichloro-1-propene=100:0
(Yield) 96%

Example 7

The same procedure as in Example 6 was carried out excepting that 0.1 g of iron (III) oxide [$Fe_2O_3$] was used instead of the iron powder, and the composition thereof was analyzed.

(Composition) 1,1,3-trichloro-1-propene:3,3,3-trichloro-1-propene=100:0
(Yield) 94%

Example 8

The same procedure as in Example 6 was carried out excepting that 0.1 g of ferrous chloride tetra-hydrate ($FeCl_2$ $4H_2O$) was used instead of the iron powder, and the composition thereof was analyzed.

(Composition) 1,1,3-trichloro-1-propene:3,3,3-trichloro-1-propene=100:0
(Yield) 94%

Example 9

The same procedure as in Example 6 was carried out excepting that 0.1 g of ferric chloride hexa-hydrate ($FeCl_3$ $6H_2O$) was used instead of the iron powder, and the composition thereof was analyzed.

(Composition) 1,1,3-trichloro-1-propene:3,3,3-trichloro-1-propene=100:0
(Yield) 88%

Example 10

The same procedure as in Example 6 was carried out excepting that 0.1 g of a copper powder was used instead of the iron powder, and the composition thereof was analyzed.

(Composition) 1,1,3-trichloro-1-propene:3,3,3-trichloro-1-propene=100:0
(Yield) 94%

Example 11

The same procedure as in Example 6 was carried out excepting that 0.1 g of cuprous oxide ($Cu_2O$) was used instead of the iron powder, and the composition thereof was analyzed.

(Composition) 1,1,3-trichloro-1-propene:3,3,3-trichloro-1-propene=100:0
(Yield) 92%

Example 12

The same procedure as in Example 6 was carried out excepting that 0.1 g of a silver powder was used instead of the iron powder, and the composition thereof was analyzed.

(Composition) 1,1,3-trichloro-1-propene:3,3,3-trichloro-1-propene=99:1
(Yield) 92%

Example 13

The same procedure as in Example 6 was carried out excepting that 0.1 g of a zinc powder was used instead of the iron powder, and the composition thereof was analyzed.

(Composition) 1,1,3-trichloro-1-propene:3,3,3-trichloro-1-propene=100:0
(Yield) 92%

Example 14

The same procedure as in Example 6 was carried out excepting that 0.1 g of zinc oxide (ZnO) was used instead of the iron powder, and the composition thereof was analyzed.
(Composition) 1,1,3-trichloro-1-propene:3,3,3-trichloro-1-propene=100:0
(Yield) 93%

Example 15

The same procedure as in Example 6 was carried out excepting that 0.1 g of a nickel powder was used instead of the iron powder, and the composition thereof was analyzed.
(Composition) 1,1,3-trichloro-1-propene:3,3,3-trichloro-1-propene=100:0
(Yield) 92%

Example 16

The same procedure as in Example 6 was carried out excepting that 0.1 g of a palladium powder was used instead of the iron powder, and the composition thereof was analyzed.
(Composition) 1,1,3-trichloro-1-propene:3,3,3-trichloro-1-propene=100:0
(Yield) 96%

Example 17

The same procedure as in Example 6 was carried out excepting that 0.1 g of a manganese powder was used instead of the iron powder, and the composition thereof was analyzed.
(Composition) 1,1,3-trichloro-1-propene:3,3,3-trichloro-1-propene=95:5
(Yield) 90%

Example 18

The same procedure as in Example 6 was carried out excepting that 0.1 g of a tin powder was used instead of the iron powder, and the composition thereof was analyzed.
(Composition) 1,1,3-trichloro-1-propene:3,3,3-trichloro-1-propene=100:0
(Yield) 98%

Example 19

The same procedure as in Example 6 was carried out excepting that 0.1 g of a bismuth powder was used instead of the iron powder, and the composition thereof was analyzed.
1,1,3-trichloro-1-propene:3,3,3-trichloro-1-propene=100:0
(Yield) 93%

Comparative Example 1

Into a 200 ml flask equipped with a reflux condenser were charged 91 g (0.5 mol) of 1,1,1,3-tetrachloropropane and 0.2 g of anhydrous ferric chloride, and a temperature rising operation was performed up to an internal temperature of 80° C. The mixture was stirred while heating at 80° C. for 4 hours. After the reaction, the product was analyzed by a gas chromatography internal standard method, to find that the yield of 1,1,3-trichloro-1-propene was 56%. The raw materials remained in an amount of 7%, and high boiling point compounds were produced in an amount of 37%.

Industrial Applicability

According to the production method of the present invention, 1,1,3-trichloro-1-propene can be simply produced with excellent yield in which the content of 1,1,1,3-tetrachloropropane and the content of high boiling point compounds are reduced.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim
1. A method of producing 1,1,3-trichloro-1-propene comprising the following steps A and B;
    Step A: 1,1,1,3-tetrachloropropane is dehydrochlorinated at a temperature between 30° C. and 50° C. in the presence of at least one base selected from the group consisting of alkali metal hydroxides and alkaline earth metal hydroxides, and a phase transfer catalyst,
    Step B: 3,3,3-trichloro-1-propene obtained in the step A is isomerized into 1,1,3-trichloro-1-propene in the presence of a metal catalyst except of ferric chloride.

2. A method of producing 1,1,1,3-trichloro-1-propene comprising the following steps A and B;
    Step A: 1,1,1,3-tetrachloropropane is dehydrochlorinated at a temperature between 30° C. and 50° C. in the presence of at least one base selected from the group consisting of alkali metal hydroxides and alkaline earth metal hydroxides, and a phase transfer catalyst, to obtain a mixture containing 1,1,3-trichloro-1-propene and 3,3,3-trichloro-1-propene;
    Step B: the mixture containing 1,1,3-trichloro-1-propene and 3,3,3-trichloro-1-propene is allowed to contact with a metal catalyst except of ferric chloride to isomerize 3,3,3-trichloro-1-propene in said mixture into 1,1,3-trichloro-1-propene.

3. The method according to claim 1, wherein the phase transfer catalyst is a quaternary ammonium salt or a quaternary phosphonium salt.

4. The method according to claim 1, wherein a base aqueous solution is used as the base in the step A.

5. The method according to claim 1, wherein a step C is carried out between the step A and the step B;
    Step C: the reaction mixture obtained in the step A is washed with an acid, then washed with water.

6. The method according to claim 5, wherein the acid is hydrochloric acid, sulfuric acid, phosphoric acid or nitric acid.

7. The method according to claim 1, wherein the metal catalyst is a metal simple body or a metal compound containing at least one metal selected from the group consisting of group VII metals, group VIII metals, group IX metals, group X metals, group XI metals, group XII metals, group XIV metals and group XV metals in the periodic table.

8. The method according to claim 1, wherein, the metal catalyst is a metal simple body or a metal compound containing at least one metal selected from the group consisting of iron, copper, zinc, silver, nickel, palladium, tin, bismuth and manganese.

9. The method according to claim 1, wherein isomerization in the step B is carried out under a temperature between 50° C. and 120° C.

10. The method according to claim 1, wherein the step A is carried out in the absence of an organic solvent.

11. The method according to claim 1, wherein the step B is carried out in the absence of an organic solvent.

12. The method according to claim 2, wherein the phase transfer catalyst is a quaternary ammonium salt or a quaternary phosphonium salt.

13. The method according to claim 2, wherein a base aqueous solution is used as the base in the step A.

14. The method according to claim 2, wherein a step C is carried out between the step A and the step B;
   Step C: the reaction mixture obtained in the step A is washed with an acid, then washed with water.

15. The method according to claim 2, wherein the metal catalyst is a metal simple body or a metal compound containing at least one metal selected from the group consisting of group VII metals, group VIII metals, group IX metals, group X metals, group XI metals, group XII metals, group XIV metals and group XV metals in the periodic table.

16. The method according to claim 2, wherein the metal catalyst is a metal simple body or a metal compound containing at least one metal selected from the group consisting of iron, copper, zinc, silver, nickel, palladium, tin, bismuth and manganese.

17. The method according to claim 2, wherein isomerization in the step B is carried out under a temperature between 50° C. and 120° C.

18. The method according to claim 2, wherein the step A is carried out in the absence of an organic solvent.

19. The method according to claim 2, wherein the step B is carried out in the absence of an organic solvent.

* * * * *